United States Patent
Chen et al.

(10) Patent No.: US 11,198,023 B2
(45) Date of Patent: Dec. 14, 2021

(54) NEUTRON CAPTURE THERAPY SYSTEM

(71) Applicant: NEUBORON MEDTECH LTD., Jiangsu (CN)

(72) Inventors: Weilin Chen, Jiangsu (CN); Yuanhao Liu, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 0 days.

(21) Appl. No.: 16/732,523

(22) Filed: Jan. 2, 2020

(65) Prior Publication Data

US 2020/0147414 A1     May 14, 2020

Related U.S. Application Data

(63) Continuation of application No. PCT/CN2018/100765, filed on Aug. 16, 2018.

(30) Foreign Application Priority Data

| Aug. 30, 2017 | (CN) | 201710760913.7 |
|---|---|---|
| Aug. 30, 2017 | (CN) | 201721095797.3 |

(51) Int. Cl.
*A61N 5/10* (2006.01)
*G21G 4/02* (2006.01)
(Continued)

(52) U.S. Cl.
CPC .......... *A61N 5/1077* (2013.01); *G21G 4/02* (2013.01); *G21K 5/04* (2013.01);
(Continued)

(58) Field of Classification Search
CPC .......... A61N 5/1077; A61N 2005/005; A61N 5/109; G21K 5/04
(Continued)

(56) References Cited

U.S. PATENT DOCUMENTS

| 2,977,297 A | * | 3/1961 | Evans | G21C 7/26 376/445 |
|---|---|---|---|---|
| 3,216,077 A | * | 11/1965 | Marchal | G21F 1/08 164/70.1 |

(Continued)

FOREIGN PATENT DOCUMENTS

| CN | 1989262 A | 6/2007 |
|---|---|---|
| CN | 103617814 A | 3/2014 |

(Continued)

OTHER PUBLICATIONS

State Intellectual Property Office of the P.R. China (ISR/CN), "International Search Report for PCT/CN2018/100765", China, Nov. 1, 2018.

*Primary Examiner* — Jack W Keith
*Assistant Examiner* — Jinney Kil
(74) *Attorney, Agent, or Firm* — Locke Lord LLP; Tim Tingkang Xia, Esq.

(57) ABSTRACT

A neutron capture therapy system, including a beam shaping assembly, and a vacuum tube and at least one cooling device. The beam shaping assembly includes a beam inlet, an accommodating cavity accommodating the vacuum tube, a moderator adjacent to an end portion of the accommodation cavity, a reflector surrounding the moderator, and a radiation shield and a beam outlet arranged in the beam shaping assembly. An end portion of the vacuum tube is provided with a target. The cooling device undergoes a nuclear reaction with a charged particle beam incident from the beam inlet to produce neutrons. The moderator decelerates the neutrons produced by the target to an epithermal neutron energy region. The reflector leads deviating neutrons back to the moderator. At least one accommodating pipeline accommodating the cooling device is arranged in the beam shaping (Continued)

assembly. A filler is filled between the cooling device and the accommodating pipeline.

16 Claims, 4 Drawing Sheets

(51) Int. Cl.
*G21K 5/04* (2006.01)
*A61N 5/00* (2006.01)

(52) U.S. Cl.
CPC .................. *A61N 2005/005* (2013.01); *A61N 2005/109* (2013.01); *A61N 2005/1094* (2013.01); *A61N 2005/1095* (2013.01)

(58) Field of Classification Search
USPC ............................................................ 600/1
See application file for complete search history.

(56) References Cited

U.S. PATENT DOCUMENTS

| | | | | |
|---|---|---|---|---|
| 4,192,714 A | * | 3/1980 | Vachon | G21C 7/06 |
| | | | | 376/220 |
| 4,280,871 A | * | 7/1981 | Hoffmann | G21C 13/036 |
| | | | | 376/277 |
| 4,891,165 A | * | 1/1990 | Suthanthiran | G21F 9/36 |
| | | | | 600/8 |
| 5,392,319 A | * | 2/1995 | Eggers | H05H 3/06 |
| | | | | 376/151 |
| 6,318,178 B1 | * | 11/2001 | Kato | G01N 29/11 |
| | | | | 73/602 |
| 2015/0287487 A1 | * | 10/2015 | Medoff | C10B 53/02 |
| | | | | 250/492.1 |
| 2016/0035444 A1 | * | 2/2016 | Singh | G21C 19/08 |
| | | | | 376/272 |
| 2016/0158579 A1 | * | 6/2016 | Liu | G21G 4/02 |
| | | | | 600/1 |
| 2016/0220839 A1 | * | 8/2016 | Kuri | H05H 6/00 |
| 2016/0270202 A1 | | 9/2016 | Shioda et al. | |

FOREIGN PATENT DOCUMENTS

| | | | | | |
|---|---|---|---|---|---|
| CN | 104511096 A | * | 4/2015 | | |
| CN | 204319539 U | * | 5/2015 | | |
| CN | 204798657 U | * | 11/2015 | | |
| CN | 205073543 U | | 3/2016 | | |
| CN | 205339881 U | * | 6/2016 | | |
| CN | 205460520 U | * | 8/2016 | | |
| CN | 106552322 A | | 4/2017 | | |
| CN | 106955427 A | | 7/2017 | | |
| CN | 109381802 A | * | 2/2019 | | |
| EP | 1895819 A1 | | 3/2008 | | |
| EP | 2648490 A1 | | 10/2013 | | |
| JP | 2006047115 A | | 2/2006 | | |
| JP | 2007242422 A | | 9/2007 | | |
| JP | 2007242422 A | * | 9/2007 | ........... A61N 5/1081 |
| JP | 2010203882 A | * | 9/2010 | | |
| RU | 2624914 C1 | | 7/2017 | | |
| WO | 2008100269 A2 | | 8/2008 | | |
| WO | WO-2016178852 A1 | * | 11/2016 | ........... C07D 217/04 |
| WO | 2017054557 A1 | | 4/2017 | | |
| WO | 2017118291 A1 | | 7/2017 | | |
| WO | 2016179381 A8 | | 12/2017 | | |

* cited by examiner

NEUTRON CAPTURE THERAPY SYSTEM

CROSS-REFERENCE TO RELATED PATENT APPLICATION

This application is a continuation application of International Application No. PCT/CN2018/100765, filed on Aug. 16, 2018, which claims priority to Chinese Patent Application No. 201710760913.7, filed on Aug. 30, 2017, and Chinese Patent Application No. 201721095797.3, filed on Aug. 30, 2017, the disclosures of which are hereby incorporated by reference.

FIELD

The present disclosure relates to a radioactive irradiation system, and more particularly to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

In an accelerator-based neutron capture therapy system, an accelerator accelerates a charged particle beam, the charged particle beam is accelerated enough to overcome the energy of the coulomb repulsion of atomic nuclei of a target in a beam shaping assembly, and nuclear reactions occur between the charged particle beam and the target to generate neutrons. Therefore, during the generation of neutrons, the target is irradiated by the accelerated charged particle beam with high power, the temperature of the target rises significantly, and as a result the service life of the target is affected.

A neutron capture therapy system with a cooling device generally includes a tubular second cooling portion configured to feed a cooling medium, a tubular third cooling portion configured to discharge the cooling medium, and a first cooling portion that is connected between the second cooling portion and the third cooling portion, is in direct contact with the target, and is configured to cool the target. In the structure, the tubular second cooling portion and the tubular third cooling portion are exposed to air, some neutrons generated from the target pass through air around the second cooling portion and the third cooling portion to be scattered outside the beam shaping assembly, and as a result effective neutron yield is reduced. In addition, the neutrons scattered outside the beam shaping assembly affect the instruments of the neutron capture therapy system and may cause radiation leakage, resulting in shortened service life of the neutron capture therapy system and radioactive hazards.

SUMMARY

To resolve the foregoing problem, one aspect of the present disclosure provides a neutron capture therapy system. The neutron capture therapy system includes a beam shaping assembly, a vacuum tube disposed in the beam shaping assembly, and at least one cooling device. The beam shaping assembly includes a beam inlet, an accommodating cavity accommodating the vacuum tube, a moderator adjacent to an end of the accommodating cavity, a reflector surrounding the moderator, a thermal neutron absorber adjacent to the moderator, a radiation shield disposed in the beam shaping assembly, and a beam outlet. A target is disposed at an end of the vacuum tube, the cooling device is configured to cool the target, the target undergoes a nuclear reaction with a charged particle beam entering through the beam inlet to generate neutrons, the neutrons form the neutron beam, the neutron beam defines a neutron beam axis, the moderator slows down the neutrons generated from the target to an epithermal neutron energy region, the reflector leads deviating neutrons back to the moderator to enhance the intensity of an epithermal neutron beam, the thermal neutron absorber assembly is configured to absorb thermal neutrons to protect superficial normal tissue from an overdose during treatment, the radiation shield is configured to shield against leaked neutrons and photons to reduce a dose to normal tissue in a non-irradiation area, at least one accommodating pipeline is disposed in the beam shaping assembly to accommodate the cooling device, and a filler is filled between the cooling device and an inner wall of the accommodating pipeline.

Compared with the related art, the technical solution disclosed in this embodiment has the following beneficial effects: The filler is filled between the cooling device and the inner wall of the accommodating pipeline to increase the service life of a neutron capture therapy system, prevent neutron leakage, and reinforce the intensity of a neutron beam.

Preferably, the filler is an aluminum alloy or a lead alloy. Compared with the technical solution in which no filler is filled between the cooling device and the inner wall of the accommodating pipeline, the technical solution recorded in this embodiment can effectively increase epithermal neutron yield, reduce fast neutron contamination, and reduce an irradiation time.

Further, the accommodating pipeline is located outside an inner wall of the accommodating cavity.

Preferably, the cooling device comprises a first cooling portion configured to cool the target, a second cooling portion and a third cooling portion located on two sides of the first cooling portion and communicated with the first cooling portion respectively, the accommodating pipeline comprises a first accommodating pipeline located between the target and the moderator, a second accommodating pipeline and a third accommodating pipeline located on two sides of the first accommodating pipeline and in communicated with the first accommodating pipeline respectively, the first cooling portion, the second cooling portion, and the third cooling portion are respectively contained in the first accommodating pipeline, the second accommodating pipeline, and the third accommodating pipeline, and the filler is filled between the second cooling portion and an inner wall of the second accommodating pipeline and between the third cooling portion and an inner wall of the third accommodating pipeline.

Further, the second cooling portion and the third cooling portion are tubular structures, the second accommodating pipeline and the third accommodating pipeline are pipes disposed to extend along a direction parallel to the neutron beam axis.

Preferably, the first cooling portion is located at an end of the vacuum tube to be in plane contact with the target, the second cooling portion and the third cooling portion extend in a direction parallel to the neutron beam axis and are respectively located on an upper side and a lower side of the vacuum tube to form a "["-shaped structure with the first cooling portion, and the second accommodating pipeline and the third accommodating pipeline extend in the direction parallel to the neutron beam axis and are respectively located on an upper side and a lower side of the vacuum tube to form a "["-shaped structure with the first accommodating pipeline.

Preferably, the first cooling portion is located at an end of the vacuum tube to be in plane contact with the target, an angle between the neutron beam axis and each of the second cooling portion and the third cooling portion is greater than 0° and less than or equal to 180°, and an angle between the neutron beam axis and each of the second accommodating pipeline and the third accommodating pipeline is greater than 0° and less than or equal to 180°.

Preferably, the second cooling portion inputs a cooling medium into the first cooling portion, and the third cooling portion outputs the cooling medium in the first cooling portion.

Further, the reflector protrudes out of the moderator on both sides of the neutron beam axis, the vacuum tube includes an extending section that is surrounded by the reflector and an insertion section that extends from the extending section and is inserted into the moderator, and the target is disposed at an end of the insertion section.

Preferably, the moderator comprises at least one conical body.

In another aspect of the present disclosure provides neutron capture therapy system, the neutron capture therapy system includes a beam shaping assembly configured to adjust a beam energy spectrum, a vacuum tube disposed in the beam shaping assembly, a target disposed at an end of the vacuum tube, at least one cooling device configured to cool the target, and at least one accommodating pipeline accommodating the cooling device, wherein a filler is filled between the cooling device and an inner wall of the accommodating pipeline.

Preferably, the filler is a lead alloy or an aluminum alloy.

Preferably, the beam shaping assembly comprises a beam inlet, an accommodating cavity for accommodating the vacuum tube, a moderator adjacent to an end of the accommodating cavity, a reflector surrounding the moderator, a radiation shield disposed in the beam shaping assembly, and a beam outlet, the vacuum tube comprises an extending section that is surrounded by the reflector and an insertion section that extends from the extending section and is inserted into the moderator, and the target is disposed at an end of the insertion section.

In yet another aspect of the present disclosure provides neutron capture therapy system, the neutron capture therapy system includes a beam shaping assembly configured to adjust a beam energy spectrum, a vacuum tube disposed in the beam shaping assembly, a target disposed at an end of the vacuum tube, at least one cooling device configured to cool the target, the cooling device comprises a first cooling portion configured to cool the target, a second cooling portion and a third cooling portion located on two sides of the first cooling portion and communicated with the first cooling portion respectively, and at least one accommodating pipeline accommodating the cooling device, the accommodating pipeline comprises a first accommodating pipeline, a second accommodating pipeline and a third accommodating pipeline, the first cooling portion, the second cooling portion, and the third cooling portion are respectively contained in the first accommodating pipeline, the second accommodating pipeline, and the third accommodating pipeline, wherein a filler is filled between the second cooling portion and an inner wall of the second accommodating pipeline and between the third cooling portion and an inner wall of the third accommodating pipeline.

Preferably, the filler is a lead alloy or an aluminum alloy.

Preferably, the second cooling portion inputs a cooling medium into the first cooling portion, and the third cooling portion outputs the cooling medium in the first cooling portion.

The "cone" or "conical body" in the embodiments of the present disclosure is a structure with an overall outer contour gradually becoming smaller from one side to the other in a direction in the drawings. One contour line of the outer contour may be a line segment, for example, a contour line corresponding to a conical body or may be an arc, for example, a contour line corresponding to the spherical body. The entire surface of the outer contour may have a smooth transition or may have nonsmooth transition. For example, many protrusions and grooves are provided in the surface of the conical body or the spherical body.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Figure 1:
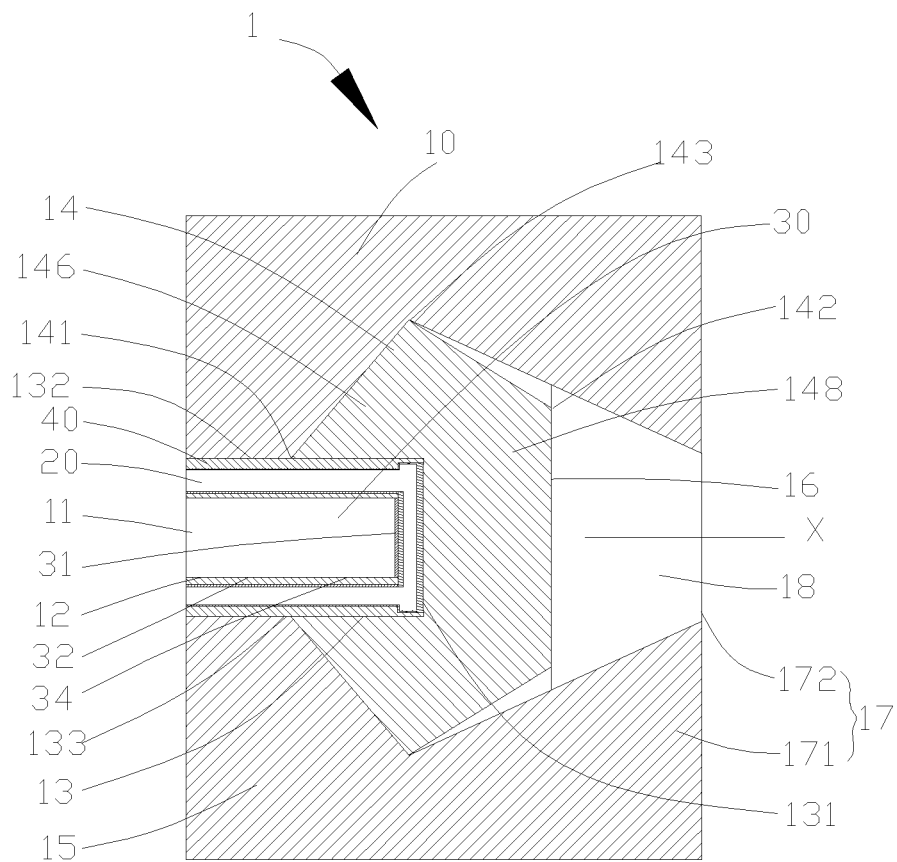
FIG. 1 is a schematic view of the neutron capture therapy system according to a first embodiment of the present disclosure, where the second cooling portion and the third cooling portion of the cooling device are parallel to the neutron beam axis.

The embodiments of the present disclosure are further described in detail below with reference to the accompanying drawings, so that those skilled in the art can implement the technical solutions according to the description.

Neutron capture therapy (NCT) has been increasingly practiced as an effective cancer curing means in recent years, and BNCT may be the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n)$^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7$Li (p, n)$^7$Be asks for more than $^9$Be (p, n)$^9$B does because of low melting point and poor thermal conductivity coefficient of the metal (lithium) target. In these embodiments of the present disclosure is $^7$Li (p, n)$^7$Be. It may be seen that the temperature of the target that is irradiated by an accelerated charged particle beam at a high energy level inevitably rises significantly, and as a result the service life of the target is affected.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux $>1\times10^9$ n/cm$^2$ s
Fast neutron contamination $<2\times10^{-13}$ Gy-cm$^2$/n
Photon contamination $<2\times10^{-13}$ Gy-cm$^2$/n
Thermal to epithermal neutron flux ratio $<0.05$
Epithermal neutron current to flux ratio $>0.7$ Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

To enable a beam shaping assembly of a neutron capture therapy system to resolve a target cooling problem and obtain relatively good neutron beam quality, referring to FIG. 1 to FIG. 4, a first embodiment of the present disclosure provides a neutron capture therapy system 1. The neutron capture therapy system 1 includes a beam shaping assembly 10, a cooling device 20 disposed in the beam shaping assembly 10, and a vacuum tube 30.

Figure 2:
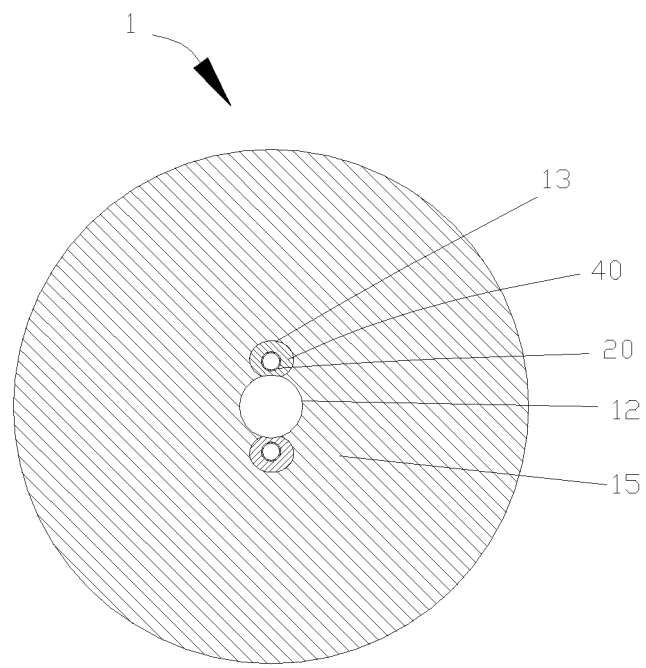
FIG. 2 is a sectional view of the neutron capture therapy system in a direction perpendicular to the neutron beam axis in FIG. 1 according to the first embodiment of the present disclosure.

As shown in FIG. 1 and FIG. 2, the beam shaping assembly 10 includes a beam inlet 11, an accommodating cavity 12 configured to accommodate the vacuum tube 30, an accommodating pipeline 13 configured to accommodate the cooling device 20, a moderator 14 adjacent to an end of the accommodating cavity 12, a reflector 15 surrounding the moderator 14, a thermal neutron absorber 16 adjacent to the moderator 14, and a radiation shield 17 disposed in the beam shaping assembly 10, and a beam outlet 18. A target 31 is disposed at an end of the vacuum tube 30, nuclear reactions occur between the target 31 and a charged particle beam that enters through the beam inlet 11 and passes through the vacuum tube 30 to generate neutrons, the neutrons form the neutron beam, and the neutron beam is emitted from the beam outlet 18 and defines one neutron beam axis X that basically coincides with the central axis of the vacuum tube 30. The moderator 14 moderate the neutrons generated from the target 31 to an epithermal neutron energy region, and the reflector 15 leads neutrons deflected from the neutron beam axis X back to the moderator 14 to enhance the intensity of an epithermal neutron beam. The reflector 15 protrudes the moderator 14 on both sides of the neutron beam axis X. The thermal neutron absorber 16 is configured to absorb thermal neutrons to protect superficial normal tissue from an overdose during treatment. The radiation shield 17 is configured to shield against leaked neutrons and photons to reduce a dose to normal tissue in a non-irradiation area.

In an accelerator-based neutron capture therapy system, an accelerator accelerates the charged particle beam. In one embodiment, the target 31 is made of lithium metal. The charged particle beam is accelerated to an energy sufficient to overcome the energy of the coulomb repulsion of atomic nuclei of the target, the $^{7}Li(p,n)^{7}Be$ nuclear reaction occurs between the charged particle beam and the target 31 to generate neutrons, the beam shaping assembly 10 can moderate the neutrons to the epithermal neutron energy region, and reduce the content of thermal neutrons and fast neutrons. The moderator 14 is made of a material with a large fast neutron reaction cross section and a small epithermal neutron reaction cross section, the reflector 15 is made of a material with high neutron reflectivity, and the thermal neutron absorber 16 is made of a material with a large thermal neutron reaction cross section. In one embodiment, the moderator 14 is made of at least one of $D_2O$, $AlF_3$, Fluental™, $CaF_2$, $Li_2CO_3$, $MgF_2$, and $Al_2O_3$, the reflector 15 is made of at least one of Pb or Ni, and the thermal neutron absorber 16 is made of $^{6}Li$.

As shown in FIG. 1, the moderator 14 is disposed a structure having at least one conical body to increase epithermal neutron fluxes. In this embodiment of the present disclosure, the moderator 14 includes two conical bodies. The moderator 14 has a first end 141, a second end 142, and a third end 143 that is located between the first end 141 and the second end 142. The cross sections of the first end 141, the second end 142, and the third end 143 are circular, and the diameters of the first end 141 and the second end 142 are less than the diameter of the third end 143. A first conical body 146 is formed between the first end 141 and the third end 143, and a second conical body 148 is formed between the third end 143 and the second end 142. In the embodiment of the present disclosure, the term "cone" or "conical body" is an element with the contour in a tapering trend from one to the other side along the direction of the neutron beam axis X. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

The radiation shield 17 includes a photon shielding 171 and a neutron shielding 172. In one embodiment, the photon shielding 171 made of lead (Pb) and the neutron shielding 172 made of polyethylene (PE).

The accommodating cavity 12 is a cylindrical cavity surrounded by the reflector 15 and the first conical body 146 of the moderator 14. The accommodating cavity 12 includes a reflector accommodating cavity 121 surrounded by the reflector 15 and a moderator accommodating cavity 122 that extends from the reflector accommodating cavity 121 and is surrounded by the moderator 14.

Figure 3:
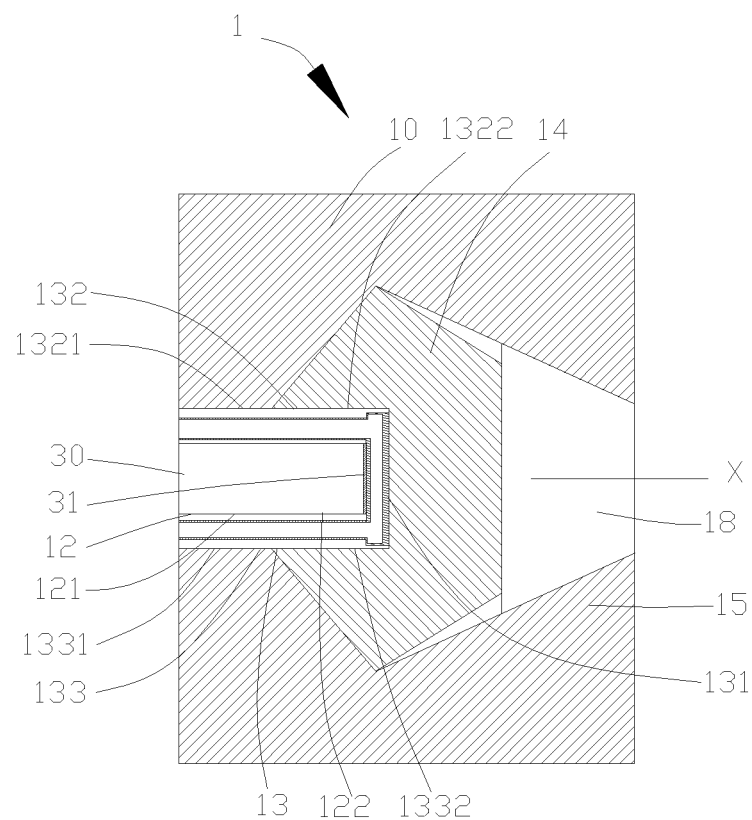
FIG. 3 is a schematic view of the neutron capture therapy system according to the first embodiment of the present disclosure, where the filler is not filled in the gap between the vacuum tube and the beam shaping assembly.

The accommodating pipeline 13 includes a first accommodating pipeline 131, a second accommodating pipeline 132 and a third accommodating pipeline 133. The second accommodating pipeline 132 and the third accommodating pipeline 133 extend along the direction of the neutron beam axis X, are located on two sides of the accommodating cavity 12, and are disposed at an interval of 180°. The first accommodating pipeline 131 is disposed in a plane perpendicular to the neutron beam axis X and is located between the target 31 and the moderator 14. The second accommodating pipeline 132 and the third accommodating pipeline 133 extend beyond the accommodating cavity 12 in the direction of the neutron beam axis X and are respectively connected with the first accommodating pipeline 131. That is, the first accommodating pipeline 131 is located at an end of the accommodating cavity 12 and is located between the target 31 and the moderator 14, and the second accommodating pipeline 132 and the third accommodating pipeline 133 are respectively located on two sides of the accommodating cavity 12 and are respectively connected with the first accommodating pipeline 131, thus, the entire accommodating pipeline 13 exhibit a "["-shaped structure. Referring to FIG. 3, the second accommodating pipeline 132 and the third accommodating pipeline 133 respectively include a second reflector accommodating pipeline 1321 and a third reflector accommodating pipeline 1331 located on an outer side of the reflector accommodating cavity 121 and a second moderator accommodating pipeline 1322 and a third moderator accommodating pipeline 1332 that respectively extend from the second reflector accommodating pipeline 1321 and the third reflector accommodating pipeline 1331 and are located on an outer side of the moderator accommodating cavity 122. In the embodiment of the present disclosure, the second accommodating pipeline 132 and the third accommodating pipeline 133 extend along the direction of the neutron beam axis X and are parallel to the neutron beam axis X, that is, an angle between the neutron beam axis X and each of the second accommodating pipeline 132 and the third accommodating pipeline 133 is 0°.

In the embodiment of the present disclosure, the second accommodating pipeline 132 and the third accommodating pipeline 133 are connected with the accommodating cavity 12, that is, part of an outer surface of the vacuum tube 30 contained in the accommodating cavity 12 is exposed in the second accommodating pipeline 132 and the third accommodating pipeline 133. In another embodiment, the second accommodating pipeline 132 and the third accommodating pipeline 133 may be not be connected with the accommodating cavity 12, that is, the second accommodating pipeline 132 and the third accommodating pipeline 133 are separated from the accommodating cavity 12 by the reflector 15 and the moderator 14. In conclusion, the second accommodating pipeline 132 and the third accommodating pipeline 133 are located outside an inner wall of the accommodating cavity 12. In the embodiment of the present disclosure, the second accommodating pipeline 132 and the third accommodating pipeline 133 are disposed to be arc-shaped pipes extending along an axial direction of the vacuum tube 30. In another embodiment, the second accommodating pipeline 132 and the third accommodating pipeline 133 may be alternatively a rectangular pipe, a triangular pipe or another polygonal pipe. In the embodiment of the present disclosure, the second accommodating pipeline 132 and the third accommodating pipeline 133 are two independent accommodating pipelines that are separated in a circumferential direction of the accommodating cavity 12. In another embodiment, the second accommodating pipeline 132 and the third accommodating pipeline 133 are connected in the circumferential direction of the accommodating cavity 12, that is, the second accommodating pipeline 132 and the third accommodating pipeline 133 are replaced by one accommodating pipeline surrounding the accommodating cavity 12.

The vacuum tube 30 includes an extending section 32 surrounding the reflector 15 and an insertion section 34 that extends from the extending section 32 and is inserted into the moderator 14. That is, the extending section 32 is contained in the reflector accommodating cavity 121, and the insertion section 34 is contained in the moderator accommodating cavity 122. The target 31 is disposed at an end of the insertion section 34 of the vacuum tube 30. In the embodiment of the present disclosure, the vacuum tube 30 is partially inserted into the moderator 14 so that the cooling device 20 can cool the target 31 in the insertion section 34 of the vacuum tube 30 and ensure the beam shaping assembly 10 to obtain a better neutron beam quality.

Figure 7:
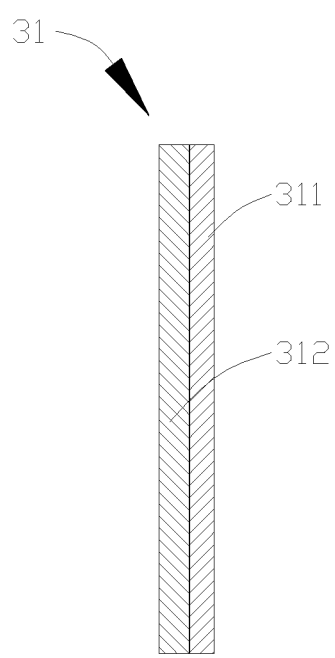
FIG. 7 is a schematic structural view of the target in the neutron capture therapy system according to an embodiment of the present disclosure.

As shown in FIG. 7, the target 31 includes a lithium target layer 311 and an antioxidation layer 312 that is located on a side of the lithium target layer 311 and is configured to prevent the lithium target layer 311 from oxidation. The antioxidation layer 312 of the target 31 is made of Al or stainless steel.

Figure 4:
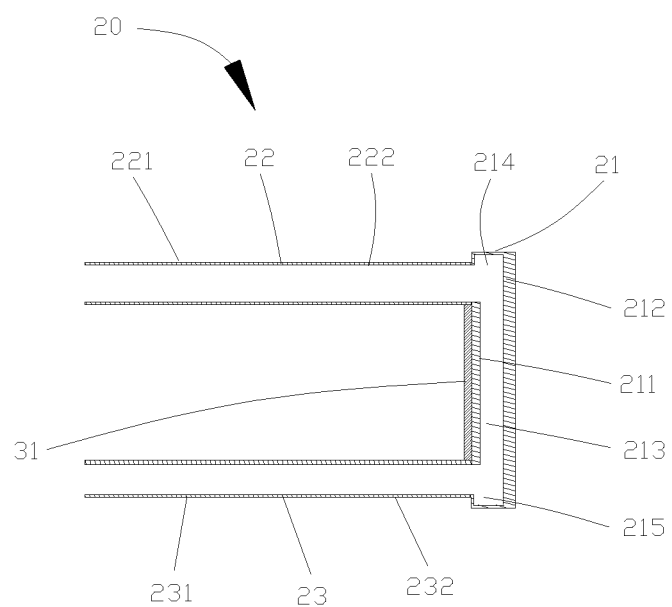
FIG. 4 is a partial enlargement view of the cooling device of the neutron capture therapy system according to the first embodiment of the present disclosure.

As shown in FIG. 4, the cooling device 20 includes a first cooling portion 21, a second cooling portion 22 and a third cooling portion 23. The first cooling portion 21 is arranged along a vertical direction and located in front of the target 31 for cooling the target 31. The second cooling portion 22 and the third cooling portion 23 extend along the direction of the neutron beam axis X and are located on two sides of the vacuum tube 30 and parallel to the neutron beam axis X. The first cooling portion 21 is connected between the second cooling portion 22 and the third cooling portion 23. The first cooling portion 21 is contained in the first accommodating pipeline 131 arranged perpendicular to the neutron beam axis X. The second cooling portion 22 and the third cooling portion 23 are respectively contained in the second accommodating pipeline 132 and the third accommodating pipeline 133 arranged along the neutron beam axis X. The second cooling portion 22 inputs a cooling medium into the first cooling portion 21, and the third cooling portion 23 outputs the cooling medium in the first cooling portion 21. The first cooling portion 21 is located between the target 31 and the moderator 14. One side of the first cooling portion 21 is in direct contact with the target 31, and the other side of the first cooling portion 21 is in contact with the moderator 14. The second cooling portion 22 and the third cooling portion 23 respectively include a first cooling section 221 and a second cooling section 231 that are located on the outer side of the reflector accommodating cavity 121 and a third cooling section 222 and a fourth cooling section 232 that respectively extend from the first cooling section 221 and the second cooling section 231 and are located on the outer side of the moderator accommodating cavity 122. The third cooling section 222 and the fourth cooling section 232 are respectively connected with the first cooling portion 21. That is, the first cooling portion 21 is located at an end of an insertion section 34 of the vacuum tube 30 and is located at one side of the target 31 and in direct contact with the target 31, the second cooling portion 22 and the third cooling portion 23 are respectively located on the upper and lower sides of the vacuum tube 30 contained in the accommodating cavity 12 and are respectively connected with the first cooling portion 21, so as to make the entire cooling device 20 is disposed a "["-shaped structure. In the embodiment of the present disclosure, the first cooling portion 21 is in plane contact with the target 31, the second cooling portion 22 and the third cooling portion 23 are both tubular structures made of copper, and the second cooling portion 22 and the third cooling portion 23 extend along the direction of the neutron beam axis X and are parallel to the neutron beam axis X, that is, an angle between the neutron beam axis X and each of the second cooling portion 22 and the third cooling portion 23 is 0°.

The first cooling portion 21 includes a first contact portion 211, a second contact portion 212, and a cooling groove 213 located between the first contact portion 211 and the second contact portion 212, the cooling medium pass through the cooling groove 213. The first contact portion 211 is direct contact with the target 31, and the second contact portion 212 may be in direct contact with the moderator 14 or indirect contact with the moderator 14 through air. The cooling groove 213 has a feeding groove 214 connected with the second cooling portion 22 and a discharge groove 215 connected with the third cooling portion 23. The first contact portion 211 is made of a thermally conductive material. An upper edge of the feeding groove 214 is located above an upper edge of the second cooling portion 22, and a lower edge of the discharge groove 215 is located below a lower edge of the third cooling portion 23. The benefit of this arrangement is that the cooling device 20 can input cooling water into the cooling groove 213 more smoothly and cool the target 31 in time, the heated cooling water can also be smoothly output from the cooling groove 213, and moreover, the water pressure of cooling water in the cooling groove 213 can be reduced.

The first contact portion 211 is made of a thermally conductive material (such as Cu, Fe, Al and other good thermal conductivity materials) or a material that can conduct heat and suppress foaming, the second contact portion 212 is made of a material that can suppresses foaming, and the material that can suppresses foaming or the material that can conduct heat and suppress foaming is made of either of Fe, Ta or V. The target 31 is irradiated by accelerated particles at a high energy level to undergo a temperature rise and radiate heat, the first contact portion 211 removes the heat, and the cooling medium that flows in the cooling groove 213 takes away the heat to cool the target 31. In the embodiment, the cooling medium is water.

Figure 6:
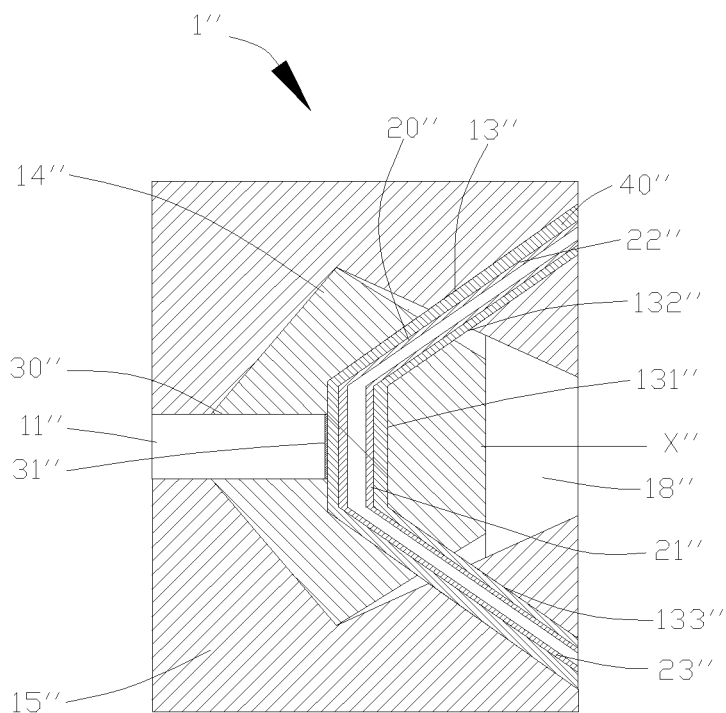
FIG. 6 is a schematic view of a neutron capture therapy system according to a third embodiment of the present disclosure, where the angle between the neutron beam axis and each of the second cooling portion and the third cooling portion of the cooling device is greater than 90°.

In the embodiment, the angle between the neutron beam axis X and each of the second accommodating pipeline 132, the third accommodating pipeline 133, the second cooling portion 22, and the third cooling portion 23 is 0°. In another embodiment, the angle between the neutron beam axis X and each of the second accommodating pipeline 132, the third accommodating pipeline 133, the second cooling portion 22, and the third cooling portion 23 can be any other angle greater than 0° and less than or equal to 180°. For example, as shown in FIG. 6, the angle between a neutron beam axis X' and each of a second accommodating pipeline 132', a third accommodating pipeline 133', a second cooling portion 22', and a third cooling portion 23' is 90°. For example, as shown in FIG. 7, the angle between a neutron beam axis X" and each of a second accommodating pipeline 132", a third accommodating pipeline 133", a second cooling portion 22", and a third cooling portion 23" is 135°.

Figure 5:
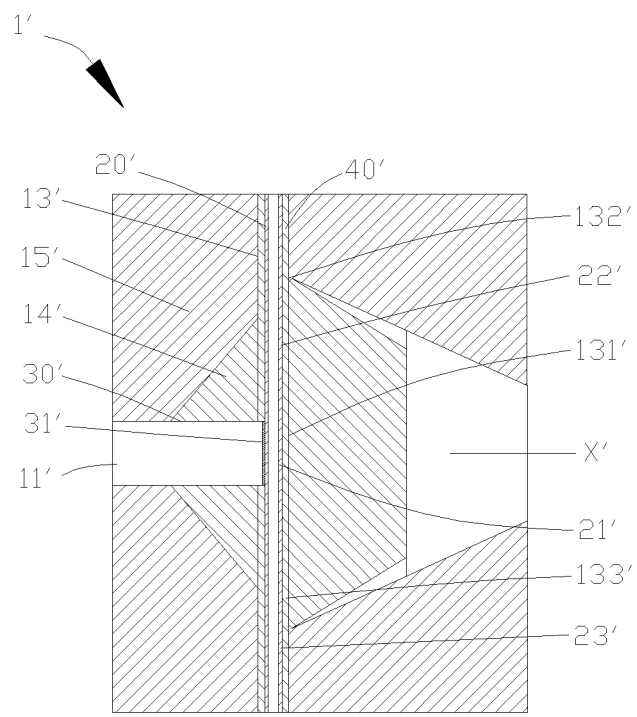
FIG. 5 is a schematic view of the neutron capture therapy system according to a second embodiment of the present disclosure, where the second cooling portion and the third cooling portion of the cooling device are perpendicular to the neutron beam axis.

As shown in FIG. 5, it disclosure a schematic diagram of a neutron capture therapy system 1' according to a second embodiment of the present disclosure. In the embodiment, the second cooling portion 22' and the third cooling portion 23' of the cooling device 20' are perpendicular to the neutron beam axis X'. That is, the cooling device 20' is disposed to an "I"-shaped structure to cool a target 31' in an inserted vacuum tube 30'. A first cooling portion 21' in the "I"-shaped cooling device 20' is the same as the first cooling portion 21 in the "["-shaped cooling device 20. Differences lie in that the second cooling portion 22', the third cooling portion 23' and the first cooling portion 21' in the "I"-shaped cooling device 20' are located in the same plane perpendicular to the neutron beam axis X', and the second cooling portion 22' and the third cooling portion 23 respectively pass through the moderator 14' along the direction perpendicular to the neutron beam axis X. That is, an angle between the neutron beam axis X' and each of the second cooling portion 22' and the third cooling portion 23' is 90°, so that the entire cooling device is a rectangle structure, that is, the above-mentioned "I"-shaped structure.

Continue to refer to FIG. 5, the accommodating pipeline 30' is also disposed to an "I"-shaped structure corresponding to the "I"-shaped cooling device 20', and a first accommodating pipeline 131' in the "I"-shaped accommodating pipeline 30' is same as the first accommodating pipeline 131 in a "["-shaped cooling pipe 30. Differences lie in that the second accommodating pipeline 132', the third accommodating pipeline 133' and the first accommodating pipeline 131' in the "I"-shaped accommodating pipeline 30' are located in the same plane perpendicular to the neutron beam axis X', and the second accommodating pipeline 132' and the third accommodating pipeline 133' respectively pass through the moderator 14' in a direction perpendicular to the neutron beam axis X'. That is, an angle between the neutron beam axis X' and each of the second accommodating pipeline 132' and the third accommodating pipeline 133' is 90°, so that the entire accommodating pipeline is rectangle structure, that is, the above-mentioned "I"-shaped structure.

As shown in FIG. 6, it disclosure a schematic diagram of a neutron capture therapy system 1" according to a third embodiment of the present disclosure. In the embodiment, the angle between the neutron beam axis X" and each of the second cooling portion 22" and the third cooling portion 23" of a cooling device 20" is greater than 90°, and a first cooling portion 21" in the cooling device 20" is same as the first cooling portion 21 in the "["-shaped the cooling device 20. A difference lies in that an angle between the neutron beam axis X" and each of the second cooling portion 22" and the third cooling portion 23" in the cooling device 20" is 135°. The first accommodating pipeline 131' in the accommodating pipeline 13" is same as the first accommodating pipeline 131 in the "["-shaped accommodating pipeline 30. A difference lies in that an angle between the neutron beam axis X' and each of the second accommodating pipeline 132" and the third accommodating pipeline 133" in the accommodating pipeline 13" is 135°.

Referring to FIG. 1, FIG. 3, FIG. 5, and FIG. 6, there are gaps between the second cooling portions 22, 22', 22" and the third cooling portions 23, 23', 23" and the inner walls of the second accommodating pipelines 132, 132', 132" and the third accommodating pipelines 133, 133', 133", respectively. A filler 40, 40', 40" is provided in the gap. The filler 40, 40', 40" is a substance such as a lead alloy or an aluminum alloy that can absorb or reflect neutrons. The filler 40, 40', 40" can reflect neutrons that are reflected or scattered into the gap into the moderator 14 or the reflector 15, thereby increasing the yield of epithermal neutrons to reduce the time that an irradiated body needs to be irradiated. In another aspect, avoiding neutrons leakage to the outside of the beam shaping assembly 10 to adversely affect the instruments of the neutron capture therapy system and improves radioactive safety. In the embodiment of the present disclosure, the content of lead in the lead alloy is greater than or equal to 85%, and the content of aluminum in the aluminum alloy is greater than or equal to 85%.

To compare impact on yield of epithermal neutrons, a contamination amount of fast neutrons, and an irradiation time when the filler 40 is respectively air or a lead alloy or an aluminum alloy, Table 1 to Table 3 are listed for detailed comparison.

Table 1 shows yield of epithermal neutrons (n/cm$^2$ mA) when the filler is respectively air, an aluminum alloy, and a lead alloy in the case of different accommodating cavity hole diameters:

TABLE 1

| Yield of epithermal neutrons (n/cm²mA) | | | | | | |
|---|---|---|---|---|---|---|
| | Accommodating cavity hole diameter (CM) | | | | | |
| | 16 CM | 18 CM | 20 CM | 22 CM | 24 CM | 26 CM |
| Air | 8.20E+07 | 7.82E+07 | 7.38E+07 | 6.97E+07 | 6.56E+07 | 6.22E+07 |
| Aluminum alloy | 8.74E+07 | 8.58E+07 | 8.40E+07 | 8.23E+07 | 8.07E+07 | 7.88E+07 |
| Lead alloy | 8.94E+07 | 8.88E+07 | 8.79E+07 | 8.69E+07 | 8.63E+07 | 8.53E+07 |

Table 2 shows a contamination amount of fast neutrons (Gy-cm2/n) when the filler is respectively air, an aluminum alloy, and a lead alloy in the case of different accommodating cavity hole diameters:

TABLE 2

| Contamination amount of fast neutrons (Gy-cm²/n) | | | | | | |
|---|---|---|---|---|---|---|
| | Accommodating cavity hole diameter (CM) | | | | | |
| | 16 CM | 18 CM | 20 CM | 22 CM | 24 CM | 26 CM |
| Air | 7.01E−13 | 7.51E−13 | 8.23E−13 | 8.95E−13 | 9.80E−13 | 1.06E−12 |
| Aluminum alloy | 6.54E−13 | 6.83E−13 | 7.17E−13 | 7.54E−13 | 7.90E−13 | 8.37E−13 |
| Lead alloy | 6.56E−13 | 6.83E−13 | 7.18E−13 | 7.52E−13 | 7.87E−13 | 8.29E−13 |

Table 3 shows an irradiation time (minute) that the irradiated body requires when the filler is respectively air, an aluminum alloy, and a lead alloy in the case of different accommodating cavity hole diameters:

TABLE 3

| Irradiation time (Min) that the irradiated body requires | | | | | | |
|---|---|---|---|---|---|---|
| | Accommodating cavity hole diameter (CM) | | | | | |
| | 16 CM | 18 CM | 20 CM | 22 CM | 24 CM | 26 CM |
| Air | 30.86 | 31.16 | 32.29 | 32.66 | 33.42 | 34.12 |
| Aluminum alloy | 29.65 | 29.07 | 30.46 | 29.42 | 29.22 | 29.39 |
| Lead alloy | 28.94 | 28.00 | 28.37 | 27.76 | 27.91 | 28.04 |

As can be learned from Table 1 to Table 3, in the case of the same diameter of the accommodating cavity hole, compared with air, when a lead alloy or an aluminum alloy is filled, the yield of epithermal neutrons is higher, the contamination amount of fast neutrons is smaller, and the required irradiation time is shorter.

The neutron capture therapy system disclosed in the present disclosure is not limited to the content in the foregoing embodiments and the structures represented in the accompanying drawings. For example, the moderator may be disposed to be a cylinder, several cooling devices may be disposed, and several accommodating pipelines are correspondingly provided. All obvious changes, replacements or modifications made to the materials, shapes, and positions of the members based on the present disclosure fall within the protection scope of the present disclosure.

Although the illustrative embodiments of the present invention have been described above in order to enable those skilled in the art to understand the present invention, it should be understood that the present invention is not to be limited to the scope of the embodiments. For those skilled in the art, as long as various changes are within the spirit and scope as defined in the present invention and the appended claims, these changes are obvious and within the scope of protection claimed by the present invention.

What is claimed is:

1. A neutron capture therapy system, comprising:
a beam shaping assembly, comprising a beam inlet, an accommodating cavity, a moderator adjacent to an end of the accommodating cavity, a reflector surrounding the moderator, a radiation shield disposed in the beam shaping assembly, and a beam outlet, wherein the moderator moderates neutrons generated from a target to an epithermal neutron energy region, the reflector leads deviating neutrons back to the moderator to enhance an intensity of an epithermal neutron beam, the radiation shield is configured to shield against leaked neutrons and photons to reduce a dose to a normal tissue in a non-irradiation area, the target is disposed at an end of the vacuum tube, the target undergoes a nuclear reaction with a charged particle beam entering through the beam inlet to generate neutrons, the neutrons form a neutron beam, and the neutron beam is emitted from the beam outlet and defines a neutron beam axis;
a vacuum tube disposed in the accommodating cavity;
at least one cooling device arranged in the beam shaping assembly, wherein the cooling device is configured to cool the target; and
at least one accommodating pipeline disposed in the beam shaping assembly to accommodate the cooling device;
wherein the cooling device comprises a first cooling portion configured to cool the target, a second cooling portion and a third cooling portion, the second cooling portion is located on one side of two sides of the first cooling portion, the third cooling portion is located on the other side of the two sides of the first cooling portion, and both the second cooling portion and the third cooling portion are connected with the first cooling portion;
wherein a filler is filled between the second cooling portion and an inner wall of the accommodating pipeline and between the third cooling portion and the inner wall of the accommodating pipeline, and the filler is a substance configured to absorb or reflect the neutrons; and wherein the accommodating pipeline comprises a first accommodating pipeline located between the target and the moderator, a second accommodating pipeline and a third accommodating pipeline, the second accommodating pipeline is located on one side of two sides of the first accommodating pipeline, the third accommodating pipeline is located on the other side of the two sides of the first accommodating pipeline, both the second accommodating pipeline and the third accommodating pipeline are connected with the first accommodating pipeline, the first cooling portion, the second cooling portion, and the third cooling portion are respectively contained in the first accommodating pipeline, the second accommodating pipeline, and the third accommodating pipeline, and the filler is filled between the second cooling portion and an inner wall of the second accommodating pipeline and between the third cooling portion and an inner wall of the third accommodating pipeline.

2. The neutron capture therapy system according to claim 1, wherein the filler is a lead alloy or an aluminum alloy.

3. The neutron capture therapy system according to claim 1, wherein the accommodating pipeline is located outside the accommodating cavity.

4. The neutron capture therapy system according to claim 1, wherein the second cooling portion and the third cooling portion are tubular structures, the second accommodating pipeline and the third accommodating pipeline are pipes disposed to extend along a direction parallel to the neutron beam axis.

5. The neutron capture therapy system according to claim 1, wherein the first cooling portion is located at the end of the vacuum tube to be in plane contact with the target, the second cooling portion and the third cooling portion extend in a direction parallel to the neutron beam axis and are respectively located on a first side and a second side opposite to the first side of the vacuum tube to form a "["-shaped structure with the first cooling portion, and the second accommodating pipeline and the third accommodating pipeline extend in the direction parallel to the neutron beam axis and are respectively located on the first side and the second side of the vacuum tube to form a "["-shaped structure with the first accommodating pipeline.

6. The neutron capture therapy system according to claim 1, wherein the second cooling portion inputs a cooling medium into the first cooling portion, and the third cooling portion outputs the cooling medium in the first cooling portion.

7. The neutron capture therapy system according to claim 1, wherein the reflector protrudes out of the moderator on both sides of the neutron beam axis, the vacuum tube comprises an extending section that is surrounded by the reflector and an insertion section that extends from the extending section and is inserted into the moderator, and the target is disposed at an end of the insertion section.

8. The neutron capture therapy system according to claim 1, wherein the moderator comprises at least one conical body.

9. The neutron capture therapy system according to claim 1, wherein the first cooling portion is arranged along a vertical direction parallel to the target and located in front of the target.

10. A neutron capture therapy system, comprising:

a beam shaping assembly configured to adjust a beam energy spectrum;

a vacuum tube disposed in the beam shaping assembly;

a target disposed at an end of the vacuum tube;

at least one cooling device configured to cool the target; and at least one accommodating pipeline accommodating the cooling device, wherein the cooling device comprises a first cooling portion configured to cool the target, a second cooling portion and a third cooling portion, the second cooling portion is located on one side of two sides of the first cooling portion, the third cooling portion is located on the other side of the two sides of the first cooling portion, and both the second cooling portion and the third cooling portion are connected with the first cooling portion;

wherein a filler is filled between the second cooling portion and an inner wall of the accommodating pipeline and between the third cooling portion and the inner wall of the accommodating pipeline, and the filler is a substance configured to absorb or reflect the neutrons; and wherein the accommodating pipeline comprises a first accommodating pipeline located between the target and the moderator, a second accommodating pipeline and a third accommodating pipeline, the second accommodating pipeline is located on one side of two sides of the first accommodating pipeline, the third accommodating pipeline is located on the other side of the two sides of the first accommodating pipeline, both the second accommodating pipeline and the third accommodating pipeline are connected with the first accommodating pipeline, the first cooling portion, the second cooling portion, and the third cooling portion are respectively contained in the first accommodating pipeline, the second accommodating pipeline, and the third accommodating pipeline, and the filler is filled between the second cooling portion and an inner wall of the second accommodating pipeline and between the third cooling portion and an inner wall of the third accommodating pipeline.

11. The neutron capture therapy system according to claim 10, wherein the filler is a lead alloy or an aluminum alloy.

12. The neutron capture therapy system according to claim 10, wherein the beam shaping assembly comprises a beam inlet, an accommodating cavity for accommodating the vacuum tube, a moderator adjacent to an end of the accommodating cavity, a reflector surrounding the moderator, a radiation shield disposed in the beam shaping assembly, and a beam outlet, the vacuum tube comprises an extending section that is surrounded by the reflector and an insertion section that extends from the extending section and is inserted into the moderator, and the target is disposed at an end of the insertion section.

13. The neutron capture therapy system according to claim 10, wherein the first cooling portion is arranged along a vertical direction parallel to the target and located in front of the target.

14. A neutron capture therapy system, comprising:
- a beam shaping assembly configured to adjust a beam energy spectrum;
- a vacuum tube disposed in the beam shaping assembly;
- a target disposed at an end of the vacuum tube;
- at least one cooling device configured to cool the target, wherein the cooling device comprises a first cooling portion configured to cool the target, a second cooling portion and a third cooling portion, the second cooling portion is located on one of two sides of the first cooling portion, the third cooling portion is located on the other side of the two sides of the first cooling portion, and both the second cooling portion and the third cooling portion are communicated with the first cooling portion; and
- at least one accommodating pipeline accommodating the cooling device, wherein the accommodating pipeline comprises a first accommodating pipeline, a second accommodating pipeline and a third accommodating pipeline, the first cooling portion, the second cooling portion, and the third cooling portion are respectively contained in the first accommodating pipeline, the second accommodating pipeline, and the third accommodating pipeline,
- wherein a filler is filled between the second cooling portion and an inner wall of the second accommodating pipeline and between the third cooling portion and an inner wall of the third accommodating pipeline, and the filler is a substance configured to absorb or reflect the neutrons.

15. The neutron capture therapy system according to claim 14, wherein the filler is a lead alloy or an aluminum alloy.

16. The neutron capture therapy system according to claim 14, wherein the second cooling portion inputs a cooling medium into the first cooling portion, and the third cooling portion outputs the cooling medium in the first cooling portion.

* * * * *